(12) United States Patent
Ozawa et al.

(10) Patent No.: US 11,933,871 B2
(45) Date of Patent: Mar. 19, 2024

(54) MRI APPARATUS AND MRI METHOD

(71) Applicant: CANON MEDICAL SYSTEMS CORPORATION, Otawara (JP)

(72) Inventors: Shinya Ozawa, Nasushiobara (JP); Takeshi Ishimoto, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/819,348

(22) Filed: Aug. 12, 2022

(65) Prior Publication Data
US 2023/0054048 A1    Feb. 23, 2023

(30) Foreign Application Priority Data
Aug. 17, 2021  (JP) .................................. 2021-132819

(51) Int. Cl.
*G01R 33/567*  (2006.01)
*A61B 5/00*  (2006.01)
*A61B 5/055*  (2006.01)

(52) U.S. Cl.
CPC .......... *G01R 33/5673* (2013.01); *A61B 5/055* (2013.01); *A61B 5/7292* (2013.01)

(58) Field of Classification Search
CPC ............ G01R 33/5673; G01R 33/5602; G01R 33/56509; G01R 33/543; A61B 5/055; A61B 5/7292; A61B 5/1135; A61B 5/7289

See application file for complete search history.

(56) References Cited

U.S. PATENT DOCUMENTS

2015/0164367 A1\*  6/2015  Furudate .............. G01R 33/543
                                                                          600/410
2016/0334486 A9   11/2016  Kuhara et al.

FOREIGN PATENT DOCUMENTS

JP         2014-121597 A      7/2014

\* cited by examiner

*Primary Examiner* — G. M. A Hyder
(74) *Attorney, Agent, or Firm* — Oblon, McClelland, Maier & Neustadt, L.L.P.

(57) ABSTRACT

According to one embodiment, MRI apparatus includes processing circuitry and an imaging device. The processing circuitry is configured to acquire at least one of body size information relating to a size of an object and breath-hold information relating to a breath-holdable time of the object. The processing circuitry is further configured to determine an imaging condition to be performed on the object based on the at least one of the body size information and the breath-hold information. The imaging device performs imaging of the object in accordance with the determined imaging condition.

14 Claims, 6 Drawing Sheets

IMAGING PRESET LIST
(PRESET LIST FOR BREATH-HOLD IMAGING)

| BODY SIZE CATEGORY | BREATH-HOLD CATEGORY | IMAGING METHOD A (C0 : T2 WEIGHTED : FSE) | | | ... | IMAGING METHOD B (C0 : T1 WEIGHTED : FE) | | | ... |
|---|---|---|---|---|---|---|---|---|---|
| | | IMAGING CONDITION SET A | | | | IMAGING CONDITION SET B | | | |
| | | FOV | NUMBER OF SLICES | MATRIX SIZE | ... | FOV | NUMBER OF SLICES | MATRIX SIZE | ... |
| LARGE (DORSOVENTRAL DIRECTION : ≧ A1cm) (LEFT-RIGHT DIRECTION : ≧ B1cm) | LONG (15~20 SEC) | IMAGING CONDITION SET (A : LARGE : LONG) | | | | IMAGING CONDITION SET (B : LARGE : LONG) | | | |
| | MEDIUM (10~15 SEC) | IMAGING CONDITION SET (A : LARGE : MEDIUM) | | | | IMAGING CONDITION SET (B : LARGE : MEDIUM) | | | |
| | SHORT (5~10 SEC) | IMAGING CONDITION SET (A : LARGE : SHORT) | | | | IMAGING CONDITION SET (B : LARGE : SHORT) | | | |
| MEDIUM (DORSOVENTRAL DIRECTION : A2~A1cm) (LEFT-RIGHT DIRECTION : B2~B1cm) | LONG (15~20 SEC) | IMAGING CONDITION SET (A : MEDIUM : LONG) | | | | IMAGING CONDITION SET (B : MEDIUM : LONG) | | | |
| | MEDIUM (10~15 SEC) | IMAGING CONDITION SET (A : MEDIUM : MEDIUM) | | | | IMAGING CONDITION SET (B : MEDIUM : MEDIUM) | | | |
| | SHORT (5~10 SEC) | IMAGING CONDITION SET (A : MEDIUM : SHORT) | | | | IMAGING CONDITION SET (B : MEDIUM : SHORT) | | | |
| SMALL (DORSOVENTRAL DIRECTION : < A2cm) (LEFT-RIGHT DIRECTION : < B2cm) | LONG (15~20 SEC) | IMAGING CONDITION SET (A : SMALL : LONG) | | | | IMAGING CONDITION SET (B : SMALL : LONG) | | | |
| | MEDIUM (10~15 SEC) | IMAGING CONDITION SET (A : SMALL : MEDIUM) | | | | IMAGING CONDITION SET (B : SMALL : MEDIUM) | | | |
| | SHORT (5~10 SEC) | IMAGING CONDITION SET (A : SMALL : SHORT) | | | | IMAGING CONDITION SET (B : SMALL : SHORT) | | | |

FIG. 4

IMAGING PRESET LIST
(PRESET LIST FOR FREE-BREATHING IMAGING)

| BODY SIZE CATEGORY | IMAGING METHOD α<br>( C0 : T2 WEIGHTED : FSE )<br>(RESPIRATORY SYNCHRONIZATION) | | | IMAGING METHOD β<br>( C0 : T1 WEIGHTED : FE )<br>(RESPIRATORY SYNCHRONIZATION) | | | ⋮ |
|---|---|---|---|---|---|---|---|
| | IMAGING CONDITION SET α | | ⋮ | IMAGING CONDITION SET β | | ⋮ | |
| | FOV | NUMBER OF SLICES | MATRIX SIZE | FOV | NUMBER OF SLICES | MATRIX SIZE | |
| LARGE<br>(DORSOVENTRAL DIRECTION : ≧ A1cm)<br>(LEFT-RIGHT DIRECTION : ≧ B1cm) | IMAGING CONDITION SET<br>( α : LARGE ) | | | IMAGING CONDITION SET<br>( β : LARGE ) | | | ⋮ |
| MEDIUM<br>(DORSOVENTRAL DIRECTION : A2∼A1cm)<br>(LEFT-RIGHT DIRECTION : B2∼B1cm) | IMAGING CONDITION SET<br>( α : MEDIUM ) | | | IMAGING CONDITION SET<br>( β : MEDIUM ) | | | ⋮ |
| SMALL<br>(DORSOVENTRAL DIRECTION : < A2cm)<br>(LEFT-RIGHT DIRECTION : < B2cm) | IMAGING CONDITION SET<br>( α : SMALL ) | | | IMAGING CONDITION SET<br>( β : SMALL ) | | | ⋮ |

FIG. 6

MRI APPARATUS AND MRI METHOD

CROSS-REFERENCE TO RELATED APPLICATIONS

This application claims the benefit of priority of Japanese Patent Application No. 2021-132819, filed Aug. 17, 2021, the entire contents of which are incorporated herein by reference.

FIELD

Embodiments described herein relate generally to an MRI (Magnetic Resonance Imaging) apparatus and an MRI method.

BACKGROUND

An MRI (Magnetic Resonance Imaging) apparatus is an imaging apparatus that magnetically excites nuclear spin of an object placed in a static magnetic field by applying an RF (Radio Frequency) pulse having the Larmor frequency and reconstructs an image on the basis of MR (Magnetic Resonance) signals emitted from the object due to the excitation.

There are various types of MRI imaging methods, such as FSE (Fast Spin Echo), EPI (Echo Planer Imaging), DWI (Diffusion Weighted Imaging), and SSFP (Steady State Free Precession). In addition, even with the same imaging method, there are various types of imaging conditions, such as imaging conditions that define parameters related to the position and size of the imaging area (that is, FOV: field of view), and imaging conditions that define parameters related to number of slices, slice spacing and matrix size (resolution).

When imaging an object such as a patient, the type of such imaging method, the imaging order of each imaging method, and the imaging conditions for each imaging method should be determined and set in the MRI apparatus in advance according to the purpose of imaging, such as examination or diagnosis.

Meanwhile, the size of the imaging area (FOV) has different appropriate values depending on the imaging region such as the head, abdomen, and legs, as well as the age of the object, and the body size of the object such as height and weight.

In addition, in the breath-hold imaging for abdomen, the imaging time should be set shorter than or equal to the breath-holdable time of the object in order to suppress artifacts caused by body movement.

Optimal values for parameters related to FOV and resolution differ depending on the body size of the object, breath-holdable time of the object, and the like. Therefore, imaging conditions that define parameters must be set for each object, and hence, the process of setting imaging conditions is extremely complicated.

Further, these imaging conditions are manually set and adjusted by a user such as an imaging technician, such that the parameters are appropriate for the object. Therefore, it takes a long time to set the imaging conditions. Further, the optimal values of the parameters to be set may vary depending on the experience and skill of the user.

BRIEF DESCRIPTION OF THE DRAWINGS

FIG. 4 is an example of a preset list for breath-hold imaging.

FIG. 6 is an example of a preset list for free-breathing imaging.

DETAILED DESCRIPTION

Hereinbelow, a description will be given of an MRI apparatus and an MRI method according to embodiments of the present invention with reference to the drawings.

In general, according to one embodiment, MRI apparatus includes processing circuitry and an imaging device. The processing circuitry is configured to acquire at least one of body size information relating to a size of an object and breath-hold information relating to a breath-holdable time of the object. The processing circuitry is further configured to determine an imaging condition to be performed on the object based on the at least one of the body size information and the breath-hold information. The imaging device performs imaging of the object in accordance with the determined imaging condition.

Figure 1:
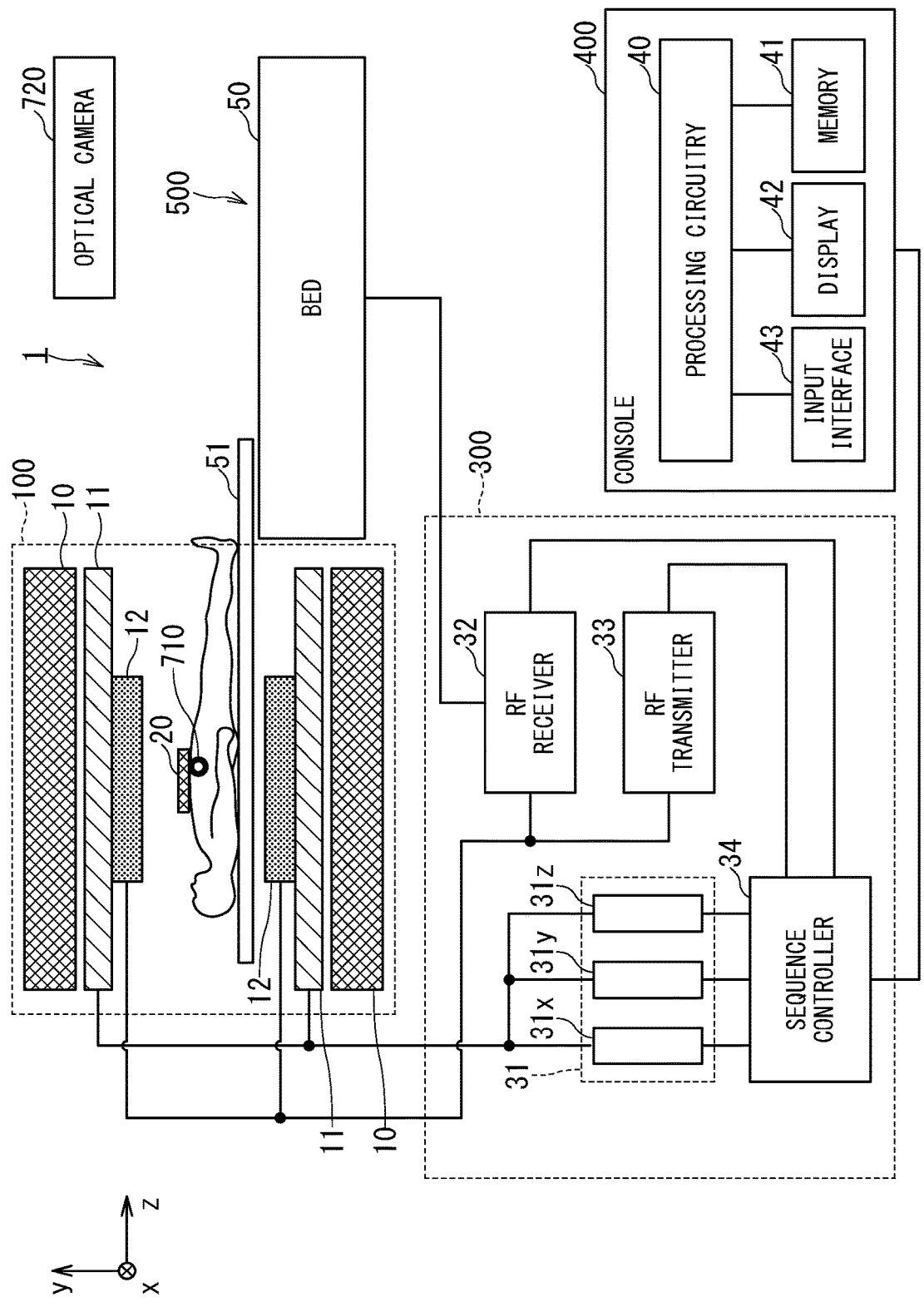
FIG. 1 is a block diagram illustrating a configuration of an MRI apparatus according to an embodiment.

FIG. 1 is a block diagram illustrating a configuration of the MRI apparatus 1 according to an embodiment. As shown in FIG. 1, an MRI apparatus 1 has a gantry (also referred to as a main body, or gantry device) 100, a control cabinet 300, a console 400, a bed 500, and an RF (Radio Frequency) coil 20.

The gantry 100 includes a static magnetic field magnet 10, a gradient coil 11, and a WB (whole body) coil 12, and these components are housed in a cylindrical housing.

The control cabinet 300 includes three gradient coil power supplies 31 (31x for an X-axis, 31y for a Y-axis, and 31z for a Z-axis), an RF receiver 32, an RF transmitter 33, and a sequence controller 34.

In this embodiment, as shown in FIG. 1, the longitudinal direction of a table 51 of the bed 500 is defined as the z-axis direction, the axial direction orthogonal to the z-axis direction and horizontal to the floor surface as the x-axis direction, and the axial direction orthogonal to the z-axis direction and vertical to the floor surface as the y-axis direction, respectively.

The console 400 includes processing circuitry 40, a memory 41, a display 42, and an input interface 43. The console 400 functions as a host computer.

The bed 500 includes a bed body 50 and a table 51.

The static magnetic field magnet 10 of the gantry 100 is substantially in the form of a cylinder, and generates a static magnetic field inside a bore into which an object, e.g., a patient, is transported. The bore is a space inside the cylindrical structure of the main body 100. The static magnetic field magnet 10 may include a superconducting coil inside, and the superconducting coil is cooled down to an extremely low temperature by liquid helium. The static magnetic field magnet 10 generates a static magnetic field by supplying the superconducting coil with an electric current provided from a non-illustrated static magnetic field power supply in an excitation mode. Afterward, the static magnetic field magnet 10 shifts to a permanent current mode, and the static magnetic field power supply is separated. Once it enters the permanent current mode, the static magnetic field magnet 10 continues to generate a static magnetic field for a long time, e.g., over one year. The static magnetic field magnet 10 may be configured of a permanent magnet.

The gradient coil 11 is also substantially in the form of a cylinder similarly to the static magnetic field magnet 10, and is fixed to the inside of the static magnetic field magnet 10. The gradient coil 11 forms gradient magnetic fields in the respective directions of the x-axis, the y-axis, and the z-axis by using electric currents supplied from the gradient coil power supplies 31$x$, 31$y$, and 31$z$.

The bed body 50 of the bed 500 can move the table 51 in the vertical direction and in the horizontal direction. For instance, the bed body 50 moves the table 51 with an object loaded thereon to a predetermined height before imaging. Afterward, when the object is to be imaged, the bed body 50 moves the table 51 in the horizontal direction so as to move the object to the inside of the bore.

The WB body coil 12 is shaped substantially in the form of a cylinder to surround the object, and is fixed to the inside of the gradient coil 11. The WB coil 12 applies RF pulses transmitted from the RF transmitter 33 to the object. The WB coil 12 receives magnetic resonance signals, i.e., MR signals emitted from the object due to excitation of hydrogen nuclei.

The MRI apparatus 1 may include the local RF coils 20 as shown in FIG. 1 in addition to the WB coil 12. Each of the local RF coils 20 is placed close to the body surface of the object. There are various types of the local RF coils 20. For instance, as the types of the local RF coils 20, as shown in FIG. 1, there are a body coil attached to the chest, abdomen, or legs of the object and a spine coil attached to the backside of the object. The local RF coils 20 may be dedicated for receiving MR signals, may be dedicated for transmitting RF pulses, or may transmit RF pulses and receive MR signals. The local RF coils 20 are configured to be attachable to and detachable from the table 51 via a cable, for instance.

The RF receiver 32 performs A/D (Analog to Digital) conversion on the channel signal from the WB coil 12 and/or the local RF coils 20, i.e., the MR signals, and outputs the converted MR signals to the sequence controller 34. The MR signals converted into digital signals are sometimes referred to as raw data.

The RF transmitter 33 generates an RF pulse based on an instruction from the sequence controller 34. The generated RF pulse is transmitted to the WB coil 12 and applied to the object. MR signals are generated from the object by the application of the RF pulse. The MR signals are received by the local RF coils 20 and/or the WB coil 12. Meanwhile, the RF receiver 32 detects channel signals, i.e., MR signals, from the WB coil 12 and the local RF coils 20, performs A/D (Analog to Digital) conversion on the detected MR signals and outputs the converted signals to the sequence controller 34. The digitally converted MR signal is also referred to as raw data.

The sequence controller 34 drives the gradient coil power supplies 31, RF transmitter 33, and RF receiver 32, under the control of console 400 to scan the object. When the sequence controller 34 receives the raw data from the RF receiver 32 after scanning, the sequence controller 34 sends the raw data to the console 400. The sequence controller 34 can be an example of an imaging device 600.

The sequence controller 34 includes non-illustrated processing circuitry. This processing circuitry is configured of hardware such as a processor for executing predetermined programs, an FPGA (Field Programmable Gate Array), and an ASIC (Application Specific Integrated Circuit).

The console 400 is configured as a computer with processing circuitry 40, a memory 41, a display 42, and an input interface 43.

The memory 41 is a storage medium that includes a ROM (Read Only Memory), RAM (Random Access Memory), and external storage devices such as HDD (Hard Disk Drive) and optical disk devices. The memory 41 stores various types of information and data, as well as various types of programs that are executed by the processor of the processing circuitry 40.

The display 42 consists of a general display output device such as a liquid crystal display or an OLED (Organic Light Emitting Diode) display, and displays various information such as images generated by the processing circuitry 40 under the control of the processing circuitry 40.

The input interface 43 consists of general input interfaces such as trackballs, switches, buttons, mice, keyboards, touchpads where input operations are made by touching the operation surface, non-contact input interfaces using optical sensors, and voice input interface. The input interface 43 outputs operation input signals corresponding to user operations to the processing circuitry 40.

The processing circuitry 40 is, e.g., a circuit equipped with a CPU (Central Processing Unit) and/or a special-purpose or general-purpose processor. The processor of the processing circuitry 40 implements various functions by executing the various programs stored in the memory 41. For example, the processor of the processing circuitry 40 reads out and executes the programs stored in the memory 41 to perform processing for easily setting the imaging conditions suitable for the object.

The processor of the processing circuitry 40 may be configured of hardware such as an FPGA and an ASIC. The various functions described below can also be implemented by such hardware. Additionally, the processing circuitry 40 can implement the various functions by combining hardware processing and software processing performed by its processor and programs.

The console 400 controls the entire MRI system 1. Specifically, the console 400 accepts imaging conditions and other various information and instructions through the operation of the input interface 43 by users such as technologists. The processing circuitry 40 causes the sequence controller 34 to execute scans based on the input imaging conditions, and reconstructs images based on the raw data transmitted from the sequence controller 34. The reconstructed image is displayed on the display 42 or stored in the memory 41.

The MRI apparatus 1 may be capable of acquiring the respiratory synchronous waveform from the respiratory sensor 710. In this case, the respiratory sensor 710 outputs the respiratory synchronous waveform of the object and provides it to the processing circuitry 40. Various types of respiratory sensors 710 are known, and any of these can be used.

The MRI apparatus 1 may also be capable of acquiring camera images captured by the optical camera 720. In this case, the optical camera 720 may be provided at a position where the image of the object placed on the table 51 before insertion into the bore of the gantry 100 can be captured. For example, the optical camera 720 may be provided on the housing of the gantry 100, or on the ceiling or walls of the room in which the MRI system 1 is installed. The optical camera 720 is composed of a CCD (Charge Coupled Device)

image sensor or a CMOS (Complementary Metal Oxide Semiconductor) image sensor. The optical camera 720 captures images of the object placed on the table 51 to generate camera images of the object, and provides the captured images to the processing circuitry 40. Further, the MRI apparatus 1 may have multiple optical cameras 720. The optical camera 720 may be configured for wide-angle imaging using a wide-angle lens, a fisheye lens, or other lenses for wide-angle imaging such that the entire body of the object can be easily captured in a single shot. In this case, the processing circuitry 40 of the console 400 may perform correction processing of distortion, caused by the lens for wide-angle imaging, on the camera image of the object acquired from the optical camera 720.

Figure 2:
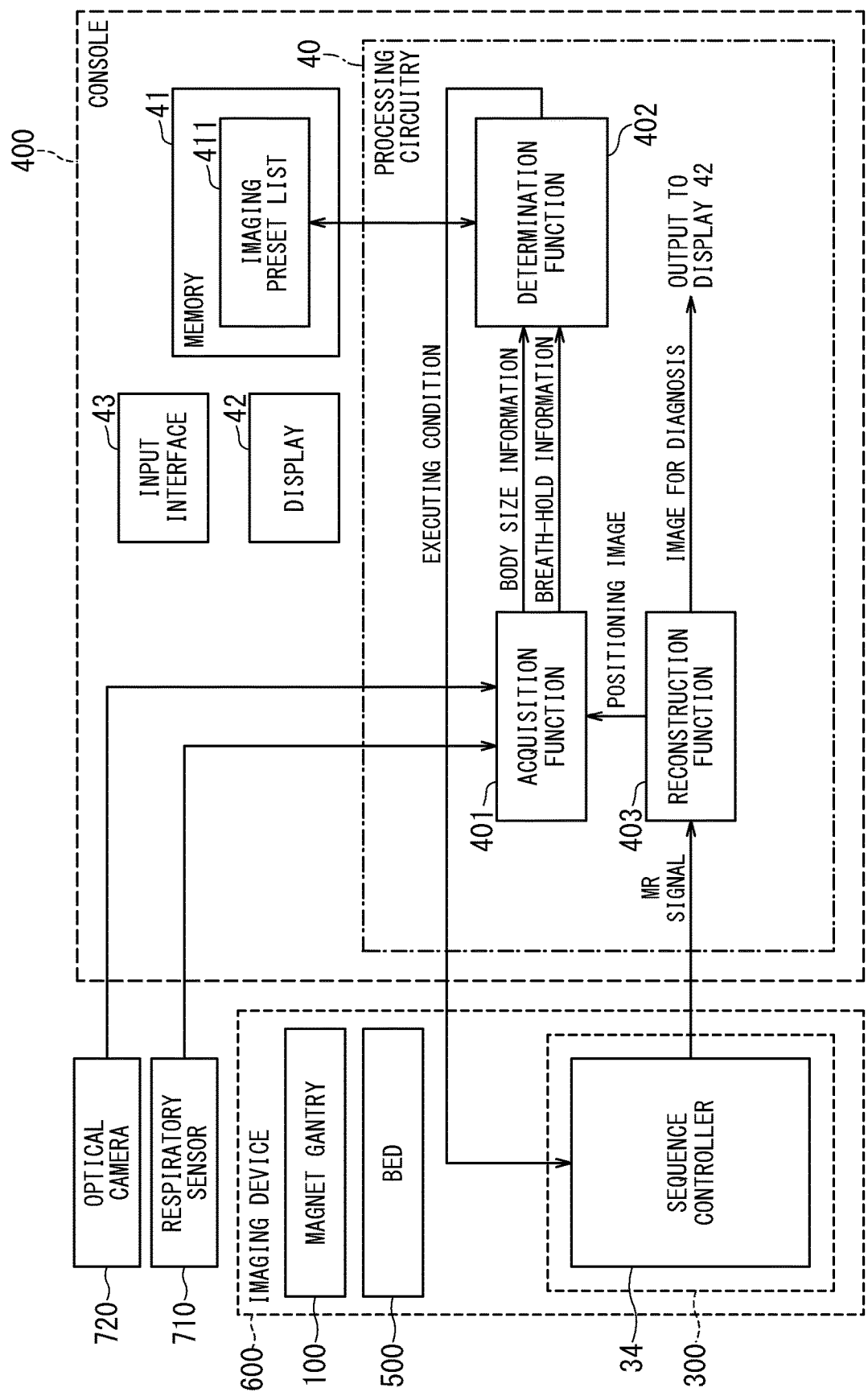
FIG. 2 is a schematic block diagram illustrating an example of functions realized by a processor of processing circuitry of a console of the MRI apparatus.

FIG. 2 is a schematic block diagram illustrating an example of functions realized by a processor of the processing circuitry 40 of the console 400 of the MRI apparatus 1.

As shown in FIG. 2, the processor of the processing circuitry 40 includes an acquisition function 401, a determination function 402, and a reconstruction function 403. Each of these functions is stored in memory 41 in the form of a program.

The acquisition function 401 acquires at least one of body size information relating to the size of the object and breath-hold information about a breath-holdable time of the object.

The determination function 402 determines an imaging condition to be performed on the object (hereinafter referred to as executing condition) based on at least one of the body size information and the breath-hold information. For example, the determination function 402 determines the executing condition of the object based on at least one of the body size information and the breath-hold information by referring to the imaging preset list 411 stored in the memory 41. The sequence controller 34 images the object according to the determined executing condition.

The imaging preset list 411 includes a plurality of imaging methods and a plurality of imaging conditions corresponding to each of the plurality of imaging methods predetermined in advance. The determination function 402 can automatically select, by referring to the imaging preset list 411, an imaging condition corresponding to the object, i.e., suitable for the object, based on at least one of the body size information and the breath-hold information of the object, thereby determining the selected imaging condition as the executing condition (imaging condition to be performed/applied).

The imaging preset list 411 includes a preset list for breath-hold imaging and a preset list for free-breathing imaging. The details of the imaging preset list 411 are described below using FIGS. 3-6.

The reconstruction function 403 receives the raw data acquired in the imaging performed according to the executing condition from the sequence controller 34, and reconstructs the image for diagnosis based on the raw data. The reconstructed image for diagnosis is displayed on the display 42 or stored in the memory 41.

Next, an example of the operation of the MRI apparatus 1 and MRI method will be described.

The MRI apparatus 1 according to this embodiment can perform imaging under holding breath (hereinafter referred to as breath-hold imaging) and imaging under free breathing (hereinafter referred to as "respiratory synchronous imaging") for the examination of abdomens. Since the breath-hold imaging is not affected by artifacts caused by the respiratory motion of the object, it is expected to acquire images of higher quality than the respiratory synchronous imaging. Therefore, when the breath-holdable time of the object is longer than the time during which the breath-hold imaging is performed, the breath-hold imaging is preferred over the respiratory synchronous imaging.

Figure 3:
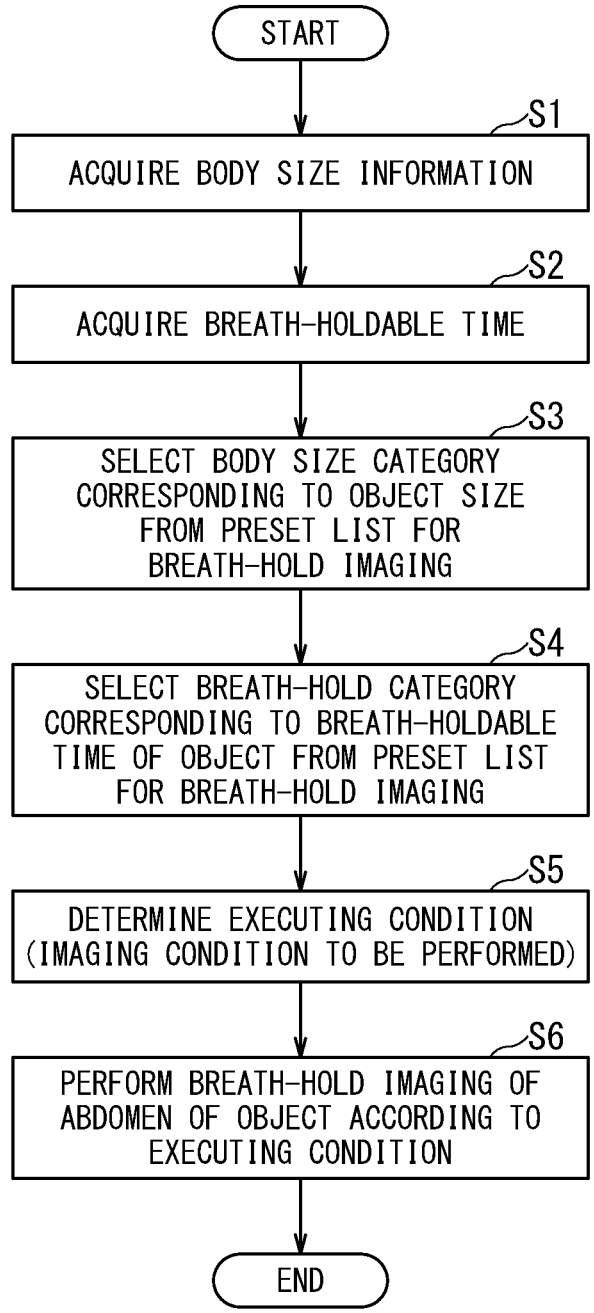
FIG. 3 is a flowchart showing an example of a procedure for easily setting imaging conditions suitable for an object when breath-hold imaging can be performed.

The procedure for attempting breath-hold imaging is explained using FIGS. 3 and 4.

FIG. 3 is a flowchart showing an example of a procedure for easily setting imaging conditions suitable for an object when breath-hold imaging can be performed. In FIG. 3, reference numerals with numbers attached to S indicates each step of the flowchart. This procedure starts when at least the inspection preset ID for breath-hold imaging is set.

First, in step S1, the acquisition function 401 acquires the body size information regarding the object size.

The object size may be acquired based on a positioning image of the object that is acquired prior to the acquisition of the image for diagnosis of the object. The positioning image of the object is acquired by imaging according to the so-called blind scan or Locator protocol, and generally includes three orthogonal cross sections. When using the positioning image, the body size information acquired by the acquisition function 401 may include the size of the object on the coronal plane, the sagittal plane, and/or the axial plane, or a combination of the thickness of the object in the dorsoventral direction and the width of the object in the left-right direction.

The object size may also be acquired based on the optical camera image of the object taken by the optical camera 720. In this case, the combination of the thickness in the dorsoventral direction of the object and the width in the left-right direction of the object can be obtained as the body size information, by using both an optical camera image of the object taken by the optical camera 720 from the side of the object such that the thickness of the object in the dorsoventral direction can be measured and an optical camera image of the object taken from the front or back such that the width in the left-right direction of the object can be measured.

The object size may be estimated from the height and weight of the object. The object size may also be input by the user via the input interface 43.

Next, in step S2, the breath-hold information regarding the breath-holdable time of the object is acquired.

The breath-holdable time of the object may be acquired based on the respiratory waveform of the object measured by the respiratory sensor 710.

For example, prior to the start of the main imaging, the object may be asked to practice breath holding, and the breath-holdable time of the object may be acquired from the respiratory waveform output by the respiratory sensor 710 during the practice.

Alternately or in addition, while performing imaging for the predetermined breath-hold imaging time during Locator imaging, the object may be requested to try to hold his or her breath during the predetermined breath-hold imaging time, and the breath-holdable time of the object can then be acquired from the respiratory waveform output by the respiratory sensor 710 during this Locator imaging. The predetermined breath-hold imaging time for this Locator imaging may be the longest breath-hold imaging time among the breath-hold category in the imaging preset list 411, which will be described later. No imaging requiring breath-hold time longer than the longest breath-hold imaging time will be performed. In such manner, all of the breath-hold imaging can be performed on the object whose breath-holdable time exceeds the longest breath-hold imaging time.

Further, the acquisition function 401 may also acquire the breath-holdable time of the object based on the moving image captured by the optical camera 720 instead of the respiratory waveform output by the respiratory sensor 710. In this case, the breath-holdable time of the object can be acquired by determining whether the object is breathing or holding his or her breath based on the movement of the abdomen of the object in the moving image captured by the optical camera 720.

The breath-holdable time of the object may be input by the user via the input interface 43.

The determination function 402 selects the imaging conditions corresponding to the object, i.e., suitable for the object, based on the body size information and the breath-hold information from the preset list for breath-hold imaging, and determines the selected imaging condition as the executing condition for the object.

FIG. 4 is an example of the preset list for breath-hold imaging.

As shown in FIG. 4, the preset list for breath-hold imaging includes multiple imaging conditions for each imaging method. Each of these multiple imaging conditions is pre-defined for each combination of multiple body size categories, which are classified into, e.g., "large," "medium," and "small" according to object size, and multiple breath-hold categories, which are classified into, e.g., "long," "medium," and "short" according to breath-holdable time of an object.

Parameters defined in imaging conditions include the number of slices, slice thickness, slice spacing, FOV, matrix size, repetition rate TR, and speed-up rate in parallel imaging.

An object with a short breath-holdable time has a shorter imaging time than an object with a long breath-holdable time. Therefore, in order to keep the imaging time within the breath-holdable time of the object, at least one parameter in the imaging conditions, such as the number of slices, slice thickness, slice spacing, matrix size, repetition rate TR, and speed-up rate in parallel imaging, may be adjusted according to the breath-holdable time of the object.

Meanwhile, the FOV and matrix size (resolution) may be adjusted according to the body size of the object. As the body size increases, not only the FOV becomes larger, but also the number of slices increases, resulting in a longer imaging time. Therefore, it is recommended to adjust at least one parameter of the imaging conditions, the number of slices, slice thickness, and slice spacing, be adjusted according to the object size.

Returning to FIG. 3, in step S3, the determination function 402 refers to the preset list for breath-hold imaging and selects a body size category corresponding to the object based on the body size information.

Next, in step S4, the determination function 402 selects a breath-hold category corresponding to the object based on the breath-hold information.

Next, in step S5, the determination function 402 determines the imaging condition corresponding to the selected body size category and breath-hold category as the executing condition.

Then, in step S6, the sequence controller 34 performs breath-hold imaging of the abdomen of the object according to the determined executing condition.

In the above manner, it is possible to easily set the imaging conditions suitable for the object when breath-hold imaging is available.

The preset list for breath-hold imaging includes pre-defined imaging conditions with appropriate parameters for each combination of the body size category and the breath-hold category for each imaging method. Therefore, according to the MRI apparatus 1, the imaging conditions for breath-hold imaging suitable for an object can be easily and automatically set based on the body size information and breath-hold information of the object. In the example shown in FIG. 4, when the imaging method A is to be performed on the object whose body size category belongs to "large" and the breath-hold category belongs to "medium," the determination function 402 can automatically set "imaging condition (A: large: medium)" as the executing condition.

Next, the case where the breath-holdable time of the object is short and breath-hold imaging is not feasible will be explained using FIGS. 5 and 6.

Figure 5:
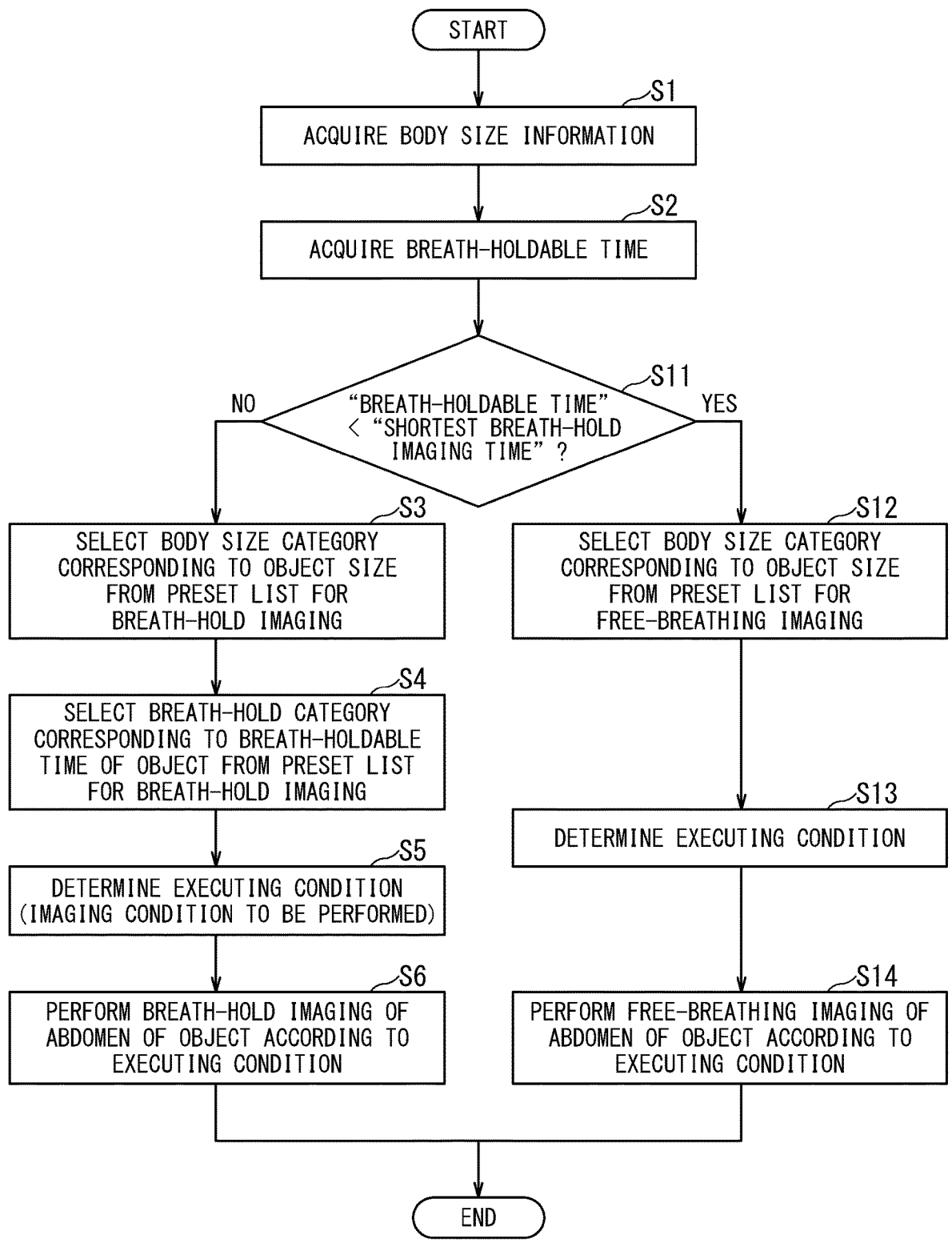
FIG. 5 is a flowchart showing an example of a procedure for easily setting imaging conditions suitable for the object in free-breathing imaging, when a breath-holdable time of the object is short and breath-hold imaging is not feasible.

FIG. 5 is a flowchart showing an example of a procedure for easily setting imaging conditions suitable for the object in free-breathing imaging when the breath-holdable time of the object is short and breath-hold imaging is not feasible. In FIG. 5, reference numerals with numbers attached to S indicates each step of the flowchart. Steps equivalent to those in FIG. 3 are marked with the same reference numerals, and duplicate explanations are omitted.

This procedure starts with the preset ID for breath-hold inspection and preset ID for free-breathing inspection are set.

When the breath-hold information about the breath-holdable time of the object is acquired in step S2, then in step S11, the determination function 402 determines whether the breath-holdable time of the object is shorter than the shortest breath-hold imaging time predetermined in the preset list for breath-hold imaging (the shortest breath-holdable time in the shortest breath-hold category, hereinafter called the shortest breath-hold imaging time).

When the breath-holdable time of the object is longer than or equal to the shortest breath-hold imaging time (NO in step S11), then the breath-hold imaging is performed in steps S3-S6 and the procedure is completed.

On the other hand, when the breath-holdable time of the object is shorter than the shortest breath-hold imaging time (YES in step S11), the procedure proceeds to step S12 and further reference is made to the preset list for free-breathing imaging, which is another preset list included in the imaging preset list 411 and is corresponding to the imaging performed under free-breathing.

FIG. 6 is an example of the preset list for free-breathing imaging.

As shown in FIG. 6, the preset list for free-breathing imaging also pre-defines multiple imaging conditions for each imaging method similar to the preset list for breath-hold imaging. Each of these multiple imaging conditions is pre-defined for multiple body size categories, which are classified into, e.g., "large," "medium," and "small" according to object size.

In step S12, the determination function 402 refers to the preset list for free-breathing imaging and selects a body size category corresponding to the object based on the body size information.

Next, in step S13, the determination function 402 determines the imaging condition corresponding to the selected body size category as the executing condition.

Then, in step S14, the sequence controller 34 performs free-breathing imaging of the abdomen of the object according to the determined executing condition.

In free-breathing imaging, the object may be imaged by the respiratory synchronous imaging in which imaging is synchronized with the respiratory waveform output by the respiratory sensor 710, or may be imaged by the diaphragm synchronous imaging using navigator echoes. In the case of diaphragm synchronous imaging, it is preferred to focus on the liver moving along with the diaphragm and perform diaphragm synchronization by monitoring the movement of the liver in live images while imaging a line profile that includes the upper edge of the liver, for example.

In the above manner, even when the breath-holdable time of the object is short and breath-hold imaging is not feasible, the imaging conditions appropriate for the object in free-breathing imaging can be easily and automatically set, and appropriate free-breathing imaging can be performed.

According to at least one of the above-described embodiments, imaging conditions suitable for the object can be easily set.

In the above-described embodiments, the term "processor" means, for example, a circuit such as a special-purpose or general-purpose CPU (Central Processing Unit), a special-purpose or general-purpose GPU (Graphics Processing Unit), an ASIC, and a programmable logic device including: an SPLD (Simple Programmable Logic Device); a CPLD (Complex Programmable Logic Device); and an FPGA. When the processor is, for example, a CPU, the processor implements various functions by reading out programs stored in a memory and executing the programs.

Additionally, when the processor is, for example, an ASIC, instead of storing the programs in the memory, the functions corresponding to the respective programs are directly incorporated as a logic circuit in the circuit of the processor. In this case, the processor implements various functions by hardware processing in which the programs incorporated in the circuit are read out and executed.

Further, the processor can also implement various functions by executing software processing and hardware processing in combination.

Although a description has been given of the case where a single processor of the processing circuitry implements each function in the above-described embodiments, the processing circuitry may be configured by combining a plurality of independent processors which implement the respective functions. When a plurality of processors are provided, the memory for storing the programs may be individually provided for each processor or one memory may collectively store the programs corresponding to the functions of all the processors.

While certain embodiments have been described, these embodiments have been presented by way of example only, and are not intended to limit the scope of the inventions. These embodiments can be implemented in various other aspects, and various omissions, substitutions, changes, and combinations of embodiments can be made without departing from the spirit of the invention. These embodiments and modifications thereof are included in the scope of the invention and the gist thereof, and are also included in the invention described in the claims and the equivalent scope thereof.

The invention claimed is:

1. An MRI apparatus comprising:
processing circuitry configured to:
acquire at least one of body size information relating to a size of an object and breath-hold information relating to a breath-holdable time of the object, and determine an imaging condition to be performed on the object based on the at least one of the body size information and the breath-hold information, wherein the processing circuitry acquires the breath-hold information based on a respiratory waveform of the object measured by a respiratory sensor; and
an imaging device imaging the object in accordance with the determined imaging condition.

2. The MRI apparatus according to claim 1, wherein the processing circuitry acquires the body size information based on a positioning image of the object that is obtained prior to obtaining an image for diagnosis of the object.

3. The MRI apparatus according to claim 1, wherein the processing circuitry acquires the body size information based on an optical camera image of the object taken by the optical camera.

4. The MRI apparatus according to claim 1, wherein the body size information acquired by the processing circuitry includes at least one of a size of the object on a coronal plane, a size of the object on a sagittal plane, a size of the object on an axial plane, a thickness of the object in a dorsoventral direction, and a width of the object in a left-right direction of the object.

5. The MRI apparatus according to claim 1, wherein the respiratory waveform is measured during imaging of a positioning image of the object, which is acquired prior to acquisition of an image for diagnosis of the object.

6. The MRI apparatus according to claim 1, wherein the processing circuitry is further configured to
refer to an imaging preset list in which a plurality of imaging methods and a plurality of imaging conditions corresponding to each of the plurality of imaging methods are predetermined; and
based on the at least one of the body size information and the breath-hold information, select an imaging condition corresponding to the object from the plurality of imaging conditions for each imaging method, and determine the selected imaging condition as the imaging condition to be performed.

7. The MRI apparatus according to claim 6, wherein:
the imaging preset list includes a preset list for breath-hold imaging corresponding to breath-hold imaging; and
each of the plurality of imaging conditions for each imaging method predetermined in the preset list for breath-hold imaging is corresponding to each combination of a plurality of body size categories classified according to the object size and a plurality of breath-hold categories classified according to the breath-holdable time of the object.

8. The MRI apparatus according to claim 7, wherein the processing circuitry is further configured to:
select a body size category corresponding to the object from the plurality of body size categories based on the acquired body size information of the object, and select a breath-hold category corresponding to the object from the plurality of breath-hold categories based on the acquired breath-hold information of the object; and
determine an imaging condition corresponding to the selected body size category and the selected breath-hold category as the imaging condition to be performed.

9. The MRI apparatus according to claim 7, wherein the processing circuitry is further configured to:
calculate a breath-holdable time of the object based on the acquired breath-hold information of the object;
compare a plurality of breath-hold imaging times corresponding to the plurality of breath-hold categories with the breath-holdable time of the object; and
when the breath-hold imaging time of the object is shorter than the shortest breath-hold imaging time of the plurality of breath-hold imaging times, further refer to a preset list for free-breathing imaging, which is another preset list included in the imaging preset list and corresponds to an imaging performed under free breathing.

10. The MRI apparatus according to claim 9, wherein:
the plurality of imaging conditions for each imaging method predetermined in the preset list for free-breathing imaging corresponds to the plurality of body size categories classified according to the object size; and
the processing circuitry is configured to select a body size category corresponding to the object from the plurality of body size categories based on the acquired body size information of the object, and determine an imaging condition corresponding to the selected body size category as the imaging condition to be performed.

11. The MRI apparatus according to claim 9, wherein the imaging performed under free breathing is imaging including either respiratory synchronous imaging, which is imaging synchronized with a signal from a respiratory sensor, or diaphragm synchronous imaging, which is imaging using a navigator echo.

12. The MRI apparatus according to claim 7, wherein each of the plurality of imaging conditions differs in at least one parameter of a number of slices, slice thickness, slice spacing, FOV, and matrix size for each body size category.

13. The MRI apparatus according to claim 7, wherein each of the plurality of imaging conditions differs in at least one parameter of a number of slices, slice thickness, slice spacing, matrix size, repetition rate TR, and speed-up rate in parallel imaging for each of the breath-hold categories.

14. An MRI method comprising:
acquiring at least one of body size information relating to a size of an object and breath-hold information relating to a breath-holdable time of the object, wherein the breath-hold information is acquired based on a respiratory waveform of the object measured by a respiratory sensor;
determining an imaging condition to be performed on the object based on the at least one of the body size information and the breath-hold information; and
imaging the object in accordance with the determined imaging condition.

* * * * *